United States Patent
Murthy

(10) Patent No.: US 7,622,138 B2
(45) Date of Patent: Nov. 24, 2009

(54) PHARMACEUTICAL COMPOSITIONS FOR DRUG DELIVERY AND METHODS OF TREATING OR PREVENTING CONDITIONS USING SAME

(75) Inventor: Yerramilli V. S. N. Murthy, Apex, NC (US)

(73) Assignee: TDEXX Laboratories, Westbrook, ME (US)

( * ) Notice: Subject to any disclaimer, the term of this patent is extended or adjusted under 35 U.S.C. 154(b) by 508 days.

(21) Appl. No.: 11/019,243

(22) Filed: Dec. 23, 2004

(65) Prior Publication Data

US 2005/0287220 A1    Dec. 29, 2005

Related U.S. Application Data

(63) Continuation-in-part of application No. 10/874,552, filed on Jun. 24, 2004.

(51) Int. Cl.
*A61K 31/704* (2006.01)
*A61K 9/14* (2006.01)

(52) U.S. Cl. .......................................... 424/488; 514/35
(58) Field of Classification Search .................. 424/488
See application file for complete search history.

(56) References Cited

U.S. PATENT DOCUMENTS

| | | | |
|---|---|---|---|
| 2,909,466 A * | 10/1959 | Neumann et al. | 514/153 |
| 4,025,620 A * | 5/1977 | Beyer et al. | 424/115 |
| 4,141,981 A * | 2/1979 | Draber et al. | 514/341 |
| 4,678,516 A * | 7/1987 | Alderman et al. | 514/781 |
| 4,814,173 A | 3/1989 | Song et al. | 424/444 |
| 4,837,008 A | 6/1989 | Rudy et al. | 424/53 |
| 4,837,213 A | 6/1989 | Caron et al. | 514/179 |
| 4,843,096 A | 6/1989 | Stiefel | 514/559 |
| 4,847,267 A | 7/1989 | Deckner et al. | 514/311 |
| 5,110,809 A | 5/1992 | Wang et al. | 514/171 |
| 5,446,070 A * | 8/1995 | Mantelle | 514/772.6 |
| 5,480,649 A | 1/1996 | Akazawa et al. | 424/449 |
| 5,516,808 A | 5/1996 | Sawaya | |
| 5,641,890 A * | 6/1997 | Wesley et al. | 44/266 |
| 5,681,849 A | 10/1997 | Richter et al. | |
| 5,736,152 A | 4/1998 | Dunn | |
| 5,856,355 A | 1/1999 | Richter et al. | |
| 5,985,259 A | 11/1999 | Cagle et al. | |
| 5,994,372 A | 11/1999 | Yaksh | |
| 6,005,001 A | 12/1999 | Richter et al. | |
| 6,018,033 A | 1/2000 | Chen et al. | 536/4.1 |
| 6,121,314 A | 9/2000 | Richter et al. | |
| 6,146,664 A | 11/2000 | Siddiqui | 424/489 |
| 6,165,987 A * | 12/2000 | Harvey | 514/30 |
| 6,214,339 B1 | 4/2001 | Pellico | 424/94.4 |
| 6,238,683 B1 * | 5/2001 | Burnett et al. | 424/405 |
| 6,436,455 B2 | 8/2002 | Zietlow et al. | 426/104 |
| 6,565,873 B1 | 5/2003 | Shefer et al. | |
| 6,645,528 B1 | 11/2003 | Straub et al. | |
| 6,669,958 B1 | 12/2003 | Trager et al. | 424/484 |
| 6,787,568 B1 | 9/2004 | Mihalik | |
| 7,220,431 B2 | 5/2007 | Sawchuk et al. | |
| 2002/0142050 A1 | 10/2002 | Straub et al. | |
| 2004/0057991 A1 | 3/2004 | Hui et al. | 424/450 |
| 2004/0138179 A1 | 7/2004 | Goldstein et al. | |
| 2004/0197408 A1 | 10/2004 | Gravett | 424/486 |
| 2004/0204471 A1* | 10/2004 | Seibert | 514/406 |
| 2004/0214753 A1 | 10/2004 | Britten et al. | |
| 2004/0220264 A1 | 11/2004 | Yu et al. | |
| 2004/0235803 A1 | 11/2004 | Britten et al. | |
| 2005/0009931 A1 | 1/2005 | Britten et al. | |
| 2005/0239722 A1 | 10/2005 | Albert et al. | |
| 2005/0287220 A1 | 12/2005 | Murthy | |
| 2006/0073198 A1 | 4/2006 | Boni et al. | |

FOREIGN PATENT DOCUMENTS

| | | |
|---|---|---|
| CN | 1383816 A | 12/2002 |
| EP | 0 081 896 | 6/1983 |
| JP | 60087215 | 5/1985 |
| WO | WO 03/034988 | 8/1998 |
| WO | WO 98/36776 | 8/1998 |
| WO | WO 99/30690 | 6/1999 |
| WO | WO 00/09117 | 2/2000 |

OTHER PUBLICATIONS

Shang-Jin He et al., Chinese Journal Of Applied Chemistry, (2202) 19(8), 742-745 (Abstract).
Handbook of Pharmaceutical Controlled Release Technology (ed. Wise) 2000, Chapters 1, 3 and 22.

* cited by examiner

*Primary Examiner*—M P Woodward
*Assistant Examiner*—Aradhana Sasan
(74) *Attorney, Agent, or Firm*—Townsend & Townsend & Crew

(57) ABSTRACT

The present invention relates to pharmaceutical compositions in the form of a gel for controlled- or sustained-release of a pharmaceutically active agent and to methods for treating or preventing or preventing a condition in an animal by administering to an animal in need thereof the pharmaceutical compositions. One particular type of condition for which the pharmaceutical compositions are useful is a microbial infection, e.g., of the skin, ear, or eye, especially for veterinary applications.

17 Claims, No Drawings

PHARMACEUTICAL COMPOSITIONS FOR DRUG DELIVERY AND METHODS OF TREATING OR PREVENTING CONDITIONS USING SAME

1. CROSS-REFERENCE TO RELATED APPLICATIONS

This application is a continuation-in-part of application Ser. No. 10/874,552, filed Jun. 24, 2004, now pending.

2. STATEMENT REGARDING FEDERALLY SPONSORED RESEARCH OR DEVELOPMENT

Not Applicable.

3. INCORPORATION-BY-REFERENCE OF MATERIAL SUBMITTED ON A COMPACT DISC

Not Applicable.

4. BACKGROUND OF THE INVENTION 4.1 Field of the Invention

The present invention relates to pharmaceutical compositions in the form of a gel for controlled- or sustained-release of a pharmaceutically active agent and to methods for treating or preventing a condition in an animal by administering to an animal in need thereof the pharmaceutical compositions. One particular type of condition for which the pharmaceutical compositions are useful is a microbial infection, e.g., of the skin, ear, or eye, especially for veterinary applications.

4.2 Description of Related Art

It is often desirable to administer drugs using controlled- or sustained-release formulations that can maintain at least a minimum therapeutic level, for example, a blood level, of the drug over extended periods of time. These controlled- or sustained-release formulations reduce the frequency of dosing, for enhanced convenience and compliance, and also reduce the severity and frequency of side effects. For example, by maintaining substantially constant blood levels and avoiding blood level fluctuations of the drug, such as are associated with conventional immediate release formulations that are administered several times a day, controlled- or sustained-release formulations can provide a better therapeutic profile than is obtainable with conventional immediate release formulations.

Known methods for controlled- or sustained-drug release include implanted devices, such as osmotic pumps, and drug dispersed in a biocompatible polymer matrix, which can be implanted, administered orally, or injected. Examples of biocompatible polymers used in such applications include poly(lactic acid) and poly(lactic acid-co-glycolic acid). The polymer typically undergoes slow hydrolysis in vivo to continually release the entrapped drug over time. The polymer degradation products are non-toxic and absorbed or metabolized by the body. For example, when the biocompatible polymer is poly(lactic acid) or poly(lactic acid-co-glycolic acid), the degradation products are the parent acids, lactic acid and glycolic acid, which are absorbed by the body.

The following patents are representative of those that discuss controlled- or sustained-drug release formulations.

U.S. Pat. No. 4,814,173 to Song et al. discloses a transmembranal pharmaceutical preparation for administering a drug to a mammal comprising a medical grade polysiloxane, a catalyst capable of forming an elastomer, a permeation enhancer, and a biologically active material. The patent disclosure focuses most on transdermal drug delivery systems, particularly transdermal patches.

U.S. Pat. No. 5,480,649 to Akazawa et al. discloses a procaterol-containing preparation for application to the skin having a drug-containing layer provided on a support and comprising a substantially water-free adhesive gel base having as essential components polyacrylic acid, a crosslinking agent, at least one lower alcohol or polyvalent alcohol, and 0.1 to 5% by weight of procaterol or a pharmaceutically acceptable salt thereof.

International Publication No. WO 03/034988 discloses compositions of a salt of a pharmacologically active compound and a lipophilic counterion and a pharmaceutically acceptable water soluble solvent that are combined together to provide an injectable composition. When injected into an animal, at least a part of the composition precipitates to form a depot that slowly releases the pharmacologically active compound over time.

The following patents are representative of those that discuss topical or otic pharmaceutical compositions.

U.S. Pat. No. 4,843,096 to Stiefel discloses a topical treatment for inflammatory acne using a non-aqueous gel containing 13-cis-retinoic acid. The patent disclosure indicates a preferred gel formulation containing about 0.05 wt % 13-cis-retinoic acid, 3 wt % hydroxypropyl cellulose, about 96.9 wt % ethanol (SDA-40B), and 0.05 wt % butylated hydroxytoluene.

U.S. Pat. No. 4,847,267 to Deckner et al. discloses a skin treatment composition and method for inhibiting free radicals in the skin comprising 6-hydroxy-2,5,7,8-tetramethylchroman-2-carboxylic acid and/or 6-ethoxy-1,2-dihydro-2,2,4-trimethyl quinoline, and optionally a stabilizer of monoethanolamine sulfite or sodium bisulfite. The skin treatment composition also includes water, at least one preservative, preferably, at least one humectant, at least one emulsifier and/or thickener, and optionally may contain one or more chelating agents, one or more gelling agents, one or more emollients, one or more solvents for the free radical inhibitor or deactivator, one or more sunscreen agents, one or more fragrances, and/or one or more coloring agents.

U.S. Pat. No. 5,110,809 to Wang et al. discloses a stable anhydrous gel formulations for topical antifungal use containing an imidazole, a steroid, a co-solvent system comprising monohydric and dihydric alcohols, and a hydroxyalkylcellulose gellant.

International Publication No. WO 00/09117 discloses topical pharmaceutical compositions containing nimesulfide, a non-steroidal anti-inflammatory agent having poor solubility in water.

U.S. Pat. No. 6,146,664 to Siddiqui discloses stable compositions of ascorbic acid in a non-aqueous or substantially anhydrous silicone vehicle containing substantially no environmental oxygen. The ascorbic acid is present as insoluble particles in the polyorganosiloxane vehicle and has a high degree of bioavailability and effectiveness, for example in topical applications to reduce wrinkles and increase collagen growth and elasticity.

U.S. Pat. No. 6,214,339 to Pellico discloses a treatment for otitis externa in cats and dogs that comprises administering a substantially non-aqueous, di-enzymatic therapeutic composition, in a liquid or gel fluid carrier. An illustrative composition contains glucose, glucose oxidase, potassium iodide, and lactoperoxidase in a fluid mixture of glycerol and propylene glycol.

U.S. Pat. No. 6,238,683 to Burnett et al. discloses anhydrous compositions for topical delivery of a medicament comprising (A) a penetration enhancer of alcohol and/or propylene glycol, (B) a humectant/solvent of polyethylene glycol, glycerin, sorbitol, and/or xylitol, (C) an anhydrous vehicle, and (D) a medicament.

The following patents are representative of those that discuss drug-containing compositions that are non-aqueous and/or gelatinous.

European Patent No. 0 081 896 B1 discloses a waterless thixotropic medicament formulation for administration to animals, especially stable semi-solid formulations of macrolide antibiotics. An exemplary formulation in an essentially anhydrous gel formulation comprising from 0.5-10 wt % of a drug, from 2-25 wt % of a hydroxylated fatty acid ester of glycerin, from 55-97.2 wt % of a glycol or glycerin, and from 0.3-15 wt % of a water-soluble polymer.

U.S. Pat. No. 4,837,008 to Rudy et al. discloses a non-aqueous paste or gel dentifrice composition for periodontal applications comprising a water-soluble, non-aqueous vehicle having dispersed therein an orally acceptable organic or inorganic peroxide and a bicarbonate salt.

U.S. Pat. No. 4,837,213 to Caron et al. discloses a pharmaceutical vehicle for administering and protecting active substances in the form of an anhydrous gel having a viscosity of at least 540 cps and comprising paraffin oil, at least one fatty acid alkyl ester, and a polyvinyldimethyl siloxane-type elastomeric silicone as a thickener.

International Publication No. WO 98/36776 and U.S. Pat. No. 6,669,958 to Trager et al. both disclose methods and compositions for the treatment of a host suffering from a cellular proliferative disease, wherein antiproliferative agents are administered in a substantially non-aqueous gel vehicle comprising at least one polar solvent in combination with one or more thickening agents.

U.S. Pat. No. 6,018,033 to Chen et al. discloses hydrophilic, hydrophobic, and thermoreversible polysaccharide gels, including hydrogels, for controlled drug delivery. Exemplary gel components copolymers of saccharose and a (meth) acrylate or of sucrose or a modified sucrose and hydrophobic poly(alkylene oxide) (meth)acrylates. The sucrose can be modified: by reaction of the sucrose with an epoxy acrylate to form a hydrophilic sucrose; by reaction first with methacryloyl chloride and then with acetyl chloride to form a hydrophobic sucrose; or by reaction first with methacryloyl chloride and then with aminocarboxylic acids to form a thermoreversible sucrose.

U.S. Pat. No. 6,436,455 to Hei et al. discloses antimicrobial and antiviral compositions containing an oxidizing species that is a reaction product of the combination of a quaternary or protonizable nitrogen compound, an oxidant compound, and a halide source at controlled proportions in an in situ aqueous, non-aqueous, gel, aerosol, solid-phase, or powdered preparation.

U.S. patent application No. US 2004/0197408 discloses formulations of a diblock copolymer having a hydrophobic block and hydrophilic block, an additive selected from an amino acid, and an oligopeptide. The formulations, when admixed with water, form drug delivery vehicles in micellar form.

There remains a need in the art, however, for drug-containing pharmaceutical compositions, suitable for topical, otic, and ophthalmic applications, that provide controlled- and/or sustained-release of the drug contained therein.

Citation of any reference in Section 4 of this application is not to be construed that such reference is prior art to the present application.

5. SUMMARY OF THE INVENTION

The invention relates to a pharmaceutical composition comprising: (i) a first organic solvent selected from the group consisting of glycerol formal, ethyl lactate, and a mixture thereof; (ii) hydroxypropyl methylcellulose; and (iii) a pharmaceutically active agent, wherein the pharmaceutical composition is in the form of a gel. Optionally, the pharmaceutical composition may further comprise a second organic solvent selected from the group consisting of glycerol, propylene glycol, poly(ethylene glycol), and mixtures thereof.

The invention also relates to a pharmaceutical composition comprising: (i) poly(ethylene glycol); (ii) a poly(acrylic acid) polymer; and (iii) a pharmaceutically active agent, wherein the pharmaceutical composition is in the form of a gel. Optionally, the pharmaceutical composition may further comprise an organic solvent selected from the group consisting of glycerol, propylene glycol, poly(ethylene glycol), and mixtures thereof.

The invention further relates to a method for treating or preventing a condition in an animal comprising topically, otically, or ophthalmically administering a therapeutically effective amount of a pharmaceutical composition of the invention. In one embodiment, the pharmaceutical composition of the invention is administered to a human, while in another embodiment the pharmaceutical composition of the invention is administered to a non-human animal.

The invention further relates to a kit containing a pharmaceutical composition of the invention.

These and other features and advantages of the present invention will become apparent from the remainder of the disclosure, in particular the following Detailed Description of the Preferred Embodiments, all of which illustrate by way of example the principles of the invention.

6. BRIEF DESCRIPTION OF THE DRAWINGS

Not Applicable.

7. DETAILED DESCRIPTION OF THE INVENTION

7.1 Definitions

As used herein, the term "gel" means a material having an average viscosity of at least about 1,000 centipoise ("cps"), preferably at least about 2,000 cps, more preferably at least about 5,000 cps, even more preferably at least about 7,500 cps, and most preferably at least about 10,000 cps, but less than about 100,000 cps, preferably less than about 75,000 cps, at 25° C. Typically, a gel exhibits quiescent and/or dynamic interaction between its components, e.g., in the form of association complexes, which are generally reversible by application of force (e.g., shear) and/or temperature to achieve flow.

As used herein, the term "polymer" means a macromolecule made up of a series of at least about 10, and preferably more, repeat units linked together. Typical polymers also have a number average molecular weight of more than about 500 g/mol. The polymer can be a homopolymer (only one type of repeat unit), a copolymer (two or more types of repeat units), a blend of homopolymers, a blend of copolymers, or a blend of one or more homopolymers and one or more copolymers.

As used herein, the term "organic solvent" means any organic compound, or a mixture of organic compounds, that is a liquid at or above about 20° C., preferably at or above about 10° C., more preferably at or above about 0° C., and most preferably at or above about <10° C. Typical organic solvents have a molecular weight of not more than about 500 g/mol and often less than about 100 g/mol. Preferred organic solvents are compounds that, when administered to an animal, do not significantly induce undue adverse effects such as excessive toxicity, irritation, or allergic response (i.e., "pharmaceutically acceptable organic solvents") commensurate with a reasonable benefit/risk ratio.

As used herein, the term "pharmaceutically active agent" means a compound that causes a pharmacological effect in an animal. Typically, the pharmacological effect is treating or preventing a condition in an animal. A pharmaceutically active agent can advantageously include a drug in its biologically active form, a pro-drug in a form such that the biologically active drug form is created in vivo in the animal, a drug metabolite, a pharmaceutically acceptable salt or ester of a biologically active drug, another therapeutically acceptable form of a biologically active drug, or some combination thereof.

The term "animal," as used herein, includes, but is not limited to, cow, horse, sheep, pig, ungulate, chimpanzee, monkey, baboon, chicken, turkey, mouse, rabbit, rat, guinea pig, dog, cat, and human.

The term "condition," as used herein, means an interruption, cessation, or disorder of a bodily function, system, or organ, and includes diseases, defects, and disorders. Representative conditions include, but are not limited to, infections such as bacterial, viral, fungal, yeast, and parasitic infections; diseases such as cancer; inflammation; diabetes; and organ failure.

The terms "effective amount" and "therapeutically effective amount," as used herein, mean an amount sufficient for treating or preventing or preventing a condition in an animal.

The phrases "treating," "treatment of," and the like, include the amelioration or cessation of a specified condition.

The phrases "preventing," "prevention of," and the like, include the avoidance of the onset of a condition.

The phrase "pharmaceutically acceptable salt," as used herein, is a salt formed from an acid and a basic nitrogen group of a pharmaceutically active agent. Illustrative salts include, but are not limited, to sulfate; citrate, acetate; oxalate; chloride; bromide; iodide; nitrate; bisulfate; phosphate; acid phosphate; isonicotinate; lactate; salicylate; acid citrate; tartrate; oleate; tannate; pantothenate; bitartrate; ascorbate; succinate; maleate; gentisinate; fumarate; gluconate; glucaronate; saccharate; formate; benzoate; glutamate; methanesulfonate; ethanesulfonate; benzenesulfonate; p-toluenesulfonate; pamoate (i.e., 1,1'-methylene-bis-(2-hydroxy-3-naphthoate)); and salts of fatty acids such as caproate, laurate, myristate, palmitate, stearate, oleate, linoleate, and linolenate salts. The term "pharmaceutically acceptable salt" also refers to a salt prepared from a pharmaceutically active agent having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia; and organic amines. Representative organic amines include, but are not limited to, unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines) such as mono-, bis-, or tris-(2-hydroxyethyl)amine, 2-hydroxy-tert-butylamine, or tris-(hydroxymethyl)methylamine, and N,N,-di-lower alkyl-N-(hydroxy lower alkyl)-amines (such as N,N,-dimethyl-N-(2-hydroxyethyl)amine or N,N,-dialkyl-N-tris-(2-hydroxyethyl)amines); N-methyl-D-glucamine; and amino acids such as arginine, lysine, and the like.

The phrases "substantially no," "substantially not," and "substantially free of," as used herein, mean less than about 5 percent by weight, preferably less than about 1 percent by weight, more preferably less than about 0.5 percent by weight, most preferably less than about 0.1 percent by weight. For example, the phrase "a pharmaceutical composition substantially free of water" means that the amount of water in the pharmaceutical composition is less than about 5 percent by weight, preferably less than about 1 percent by weight, more preferably less than about 0.5 percent by weight, most preferably less than about 0.1 percent by weight of the pharmaceutical composition.

7.2 Pharmaceutical Composition Comprising Hydroxypropyl Methylcellulose; Glycerol Formal, Ethyl Lactate, or a Mixture thereof; and a Pharmaceutically Active Agent The present invention relates to a pharmaceutical composition comprising: (i) a first organic solvent selected from the group consisting of glycerol formal, ethyl lactate, and a mixture thereof; (ii) hydroxypropyl methylcellulose; and (iii) a therapeutically effective amount of a pharmaceutically active agent, wherein the pharmaceutical composition is in the form of a gel.

In one embodiment, the pharmaceutical composition further comprises a second organic solvent selected from the group consisting of glycerol, propylene glycol, poly(ethylene glycol), and a mixture thereof.

The hydroxypropyl methylcellulose has an average molecular weight sufficiently high such that the hydroxypropyl methylcellulose, the organic solvent(s), and the pharmaceutically active agent form a gel when they are combined.

In one embodiment, the number average molecular weight of the hydroxypropyl methylcellulose is at least about 7,500 g/mol.

In another embodiment, the number average molecular weight of the hydroxypropyl methylcellulose is at least about 10,000 g/mol.

In another embodiment, the number average molecular weight of the hydroxypropyl methylcellulose is at least about 20,000 g/mol.

In another embodiment, the number average molecular weight of the hydroxypropyl methylcellulose is at least about 30,000 g/mol.

In another embodiment, the number average molecular weight of the hydroxypropyl methylcellulose is from about 7,500 to about 1,000,000 g/mol.

In another embodiment, the number average molecular weight of the hydroxypropyl methylcellulose is from about 10,000 to about 1,000,000 g/mol.

In another embodiment, the number average molecular weight of the hydroxypropyl methylcellulose is from about 20,000 to about 1,000,000 g/mol.

In another embodiment, the number average molecular weight of the hydroxypropyl methylcellulose is from about 30,000 to about 1,000,000 g/mol.

In one embodiment, the hydroxypropyl methylcellulose may be crosslinked. Without wishing to be bound by theory, it is believed that crosslinking the hydroxypropyl methylcellulose facilitates gel formation.

In another embodiment, the hydroxypropyl methylcellulose is substantially not crosslinked.

In one embodiment, the amount of hydroxypropyl methylcellulose in the pharmaceutical composition of the invention ranges from about 1 to about 10 wt % of the pharmaceutical composition.

In another embodiment, the amount of hydroxypropyl methylcellulose in the pharmaceutical composition of the invention ranges from about 2 to about 6 wt % of the pharmaceutical composition.

In another embodiment, the amount of hydroxypropyl methylcellulose in the pharmaceutical composition of the invention ranges from about 2 to about 5 wt % of the pharmaceutical composition.

In another embodiment, the amount of hydroxypropyl methylcellulose in the pharmaceutical composition of the invention ranges from about 3 to about 6 wt % of the pharmaceutical composition.

In another embodiment, the amount of hydroxypropyl methylcellulose in the pharmaceutical composition of the invention ranges from about 3 to about 4 wt % of the pharmaceutical composition.

By varying the amount of hydroxypropyl methylcellulose, the viscosity of the pharmaceutical composition can be varied. Typically, the greater the amount of hydroxypropyl methylcellulose, the higher the resulting viscosity of the pharmaceutical composition.

One of ordinary skill in the art will recognize, however, that the amount of hydroxypropyl methylcellulose in the pharmaceutical compositions of the invention can vary widely depending on, inter alia, its molecular weight, the organic solvent(s) present, the pharmaceutically active agent present, and/or other additional components present in the pharmaceutical composition.

The first organic solvent and the optional second organic solvent can include small amounts of impurities. Typically, the organic solvent(s) has(have) a purity of greater than about 95 percent by weight, preferably greater than about 97 percent by weight, more preferably greater than about 98 percent by weight, and most preferably greater than about 99 percent by weight.

In one embodiment, the first organic solvent comprises glycerol formal. In another embodiment, the first organic solvent is glycerol formal.

In another embodiment, the first organic solvent comprises ethyl lactate. In another embodiment, the first organic solvent is ethyl lactate.

In one embodiment, the second organic solvent comprises poly(ethylene glycol). In another embodiment, the poly(ethylene glycol) has a molecular weight not more than about 500 g/mol. In another embodiment, the poly(ethylene glycol) has a molecular weight of about 400 g/mol.

In another embodiment, the second organic solvent is poly(ethylene glycol). In another embodiment, the poly(ethylene glycol) has a molecular weight not more than about 500 g/mol. In another embodiment, the poly(ethylene glycol) has a molecular weight of about 400 g/mol.

In another embodiment, the second organic solvent comprises propylene glycol. In another embodiment, the second organic solvent is propylene glycol.

In another embodiment, the second organic solvent comprises glycerol. In another embodiment, the second organic solvent is glycerol.

The total amount of organic solvent (i.e., the first organic solvent plus the second organic solvent, if present) typically ranges from about 10 to about 98 wt % of the pharmaceutical composition.

In another embodiment, the total amount of organic solvent is from about 20 to about 98 wt % of the pharmaceutical composition.

In another embodiment, the total amount of organic solvent is from about 25 to about 90 wt % of the pharmaceutical composition.

In another embodiment, the total amount of organic solvent is from about 35 to about 95 wt % of the pharmaceutical composition.

In another embodiment, the total amount of organic solvent is from about 45 to about 90 wt % of the pharmaceutical composition.

In another embodiment, the total amount of organic solvent is from about 50 to about 95 wt % of the pharmaceutical composition.

In another embodiment, the total amount of organic solvent is from about 60 to about 90 wt % of the pharmaceutical composition.

In another embodiment, the total amount of organic solvent is from about 55 to about 95 wt % of the pharmaceutical composition.

In another embodiment, the total amount of organic solvent is from about 70 to about 98 wt % of the pharmaceutical composition.

The amount of the second organic solvent, when present, can be up to about 50 wt % of the total amount of organic solvent.

In one embodiment, the pharmaceutical composition contains substantially no second organic solvent.

In another embodiment, the amount of the second organic solvent is up to about 40 wt % of the total amount of organic solvent.

In another embodiment, the amount of the second organic solvent is up to about 30 wt % of the total amount of organic solvent.

In another embodiment, the amount of the second organic solvent is up to about 20 wt % of the total amount of organic solvent.

In another embodiment, the amount of the second organic solvent is up to about 10 wt % of the total amount of organic solvent.

In another embodiment, the amount of the second organic solvent is up to about 5 wt % of the total amount of organic solvent.

In another embodiment, the amount of the second organic solvent is from about 5 wt % to about 40 wt % of the total amount of organic solvent.

In another embodiment, the amount of the second organic solvent is from about 10 wt % to about 30 wt % of the total amount of organic solvent.

In another embodiment, the amount of the second organic solvent is from about 5 wt % to about 25 wt % of the total amount of organic solvent.

In another embodiment, the amount of the second organic solvent is from about 10 wt % to about 20 wt % of the total amount of organic solvent.

In one embodiment, the first organic solvent is glycerol formal and the second organic solvent is glycerol.

In another embodiment, the glycerol formal and glycerol are present in the pharmaceutical composition in a volume ratio of about 90:10.

In one embodiment, the pharmaceutical composition comprises hydroxypropyl methyl cellulose, glycerol, and glycerol formal.

In another embodiment, the pharmaceutical composition comprises from about 0.2 to about 7 wt % hydroxypropyl methyl cellulose, from about 3 to about 20 wt % glycerol, and from about 65 to about 86 wt % glycerol formal.

In another embodiment, the pharmaceutical composition comprises about 4 wt % hydroxypropyl methyl cellulose, from about 9 to about 10 wt % glycerol, and from about 78 to about 85 wt % glycerol formal.

In another embodiment, the first organic solvent is ethyl lactate and the second organic solvent is glycerol.

In another embodiment, the ethyl lactate and glycerol are present in the pharmaceutical composition in a volume ratio from about 95:5 to about 75:25.

In one embodiment, the pharmaceutical composition comprises hydroxypropyl methyl cellulose, glycerol, and ethyl lactate.

In another embodiment, the pharmaceutical composition comprises from about 0.2 to about 7 wt % hydroxypropyl methyl cellulose, from about 3 to about 20 wt % glycerol, and from about 65 to about 86 wt % ethyl lactate.

In another embodiment, the pharmaceutical composition comprises about 4 wt % hydroxypropyl methyl cellulose, from about 9 to about 10 wt % glycerol, and from about 78 to about 85 wt % ethyl lactate.

Any pharmaceutically active agent can be used in this pharmaceutical composition of the invention.

The pharmaceutical composition of the invention can be prepared by simply adding the pharmaceutically active agent(s) to the glycerol formal and/or ethyl lactate, as well as the second organic solvent, if present (typically about 90% of the total amount of the organic solvent desired in the final pharmaceutical composition), and agitating the resulting mixture until the pharmaceutically active agent(s) dissolve(s). One or more optional additive components can simultaneously and/or sequentially be added and the mixture agitated until the additive component(s) dissolve(s). HPMC is then added followed by additional solvent, to provide the desired concentration of the pharmaceutically active agent(s) in the pharmaceutical composition. Optionally, the solvent is warmed to a temperature of about 40° C. before the HMPC is added. Once all the desired components are added, the resulting solution can then be homogenized, e.g., for about 1 to about 10 minutes, to form a uniform pharmaceutical composition. Without being bound to theory, it is believed that longer homogenization time and higher homogenization speeds result in a pharmaceutical composition having reduced viscosity. Following homogenization, the composition can be allowed to sit undisturbed until a gel is formed. One skilled in the art will readily recognize, however, that modifications to the above-described method for preparing the pharmaceutical compositions of the invention are possible, for example the order of adding the components to the solvent(s) can be changed.

7.3 Pharmaceutical Composition Comprising Poly(Acrylic Acid), Poly(Ethylene Glycol) and a Pharmaceutically Active Agent Another aspect of the present invention relates to a pharmaceutical composition comprising: (i) poly(ethylene glycol); (ii) a poly(acrylic acid) polymer; and (iii) a therapeutically effective amount of a pharmaceutically active agent, wherein the pharmaceutical composition is in the form of a gel.

In one embodiment, the pharmaceutical compositions further comprises an organic solvent selected from the group consisting of glycerol, propylene glycol, and a mixture thereof.

The poly(acrylic acid) polymer used in the pharmaceutical compositions of the invention has an average molecular weight sufficiently high such that the poly(acrylic acid) polymer, the poly(ethylene glycol), the optional organic solvents, and the pharmaceutically active agent form a gel when they are combined.

In one embodiment, the number average molecular weight of the poly(acrylic acid) polymer is at least about 7,500 g/mol.

In another embodiment, the number average molecular weight of the poly(acrylic acid) polymer is at least about 10,000 g/mol.

In another embodiment, the number average molecular weight of the poly(acrylic acid) polymer is at least about 20,000 g/mol.

In another embodiment, the number average molecular weight of the poly(acrylic acid) polymer is at least about 30,000 g/mol.

In another embodiment, the number average molecular weight of the poly(acrylic acid) polymer is from about 7,500 to about 1,000,000 g/mol.

In another embodiment, the number average molecular weight of the poly(acrylic acid) polymer is from about 10,000 to about 1,000,000 g/mol.

In another embodiment, the number average molecular weight of the poly(acrylic acid) polymer is from about 20,000 to about 1,000,000 g/mol.

In another embodiment, the number average molecular weight of the poly(acrylic acid) polymer is from about 30,000 to about 1,000,000 g/mol.

In one embodiment, the poly(acrylic acid) polymer used in the pharmaceutical compositions of the invention is substantially not crosslinked.

In another embodiment, the polymer used in the pharmaceutical compositions of the invention comprises crosslinked poly(acrylic acid), e.g., such as commercially available under the tradename Carbomer™ or Carbopol® from Noveon, Inc., of Cleveland, Ohio. In another embodiment, the polymer(s) used in the pharmaceutical compositions according to the invention comprises Carbomer™ 941 or Carbopol® 941. Without wishing to be bound by theory, it is believed that certain crosslinked polymers facilitate gel formation.

In one embodiment, the amount of poly(acrylic acid) polymer ranges from about 0.1 to about 2 wt % of the pharmaceutical composition.

In another embodiment, the amount of poly(acrylic acid) polymer ranges from about 0.1 to about 1 wt % of the pharmaceutical composition.

In another embodiment, the amount of poly(acrylic acid) polymer ranges from about 0.2 to about 0.6 wt % of the pharmaceutical composition.

In another embodiment, the amount of poly(acrylic acid) polymer is about 0.4 wt % of the pharmaceutical composition.

One of ordinary skill in the art will recognize, however, that the amount of poly(acrylic acid) polymer in the pharmaceutical compositions of the invention can vary widely depending on, inter alia, the level of polymer crosslinking, the molecular weights of the polymer, the molecular weights of the poly(ethylene glycol), the optional organic solvent(s) present, the pharmaceutically active agent present, and/or other additional components present in the pharmaceutical composition.

The poly(ethylene glycol) and the optional organic solvent can include small amounts of impurities. Typically, poly(ethylene glycol) and the optional organic solvent have a purity of greater than about 95 percent by weight, preferably greater than about 97 percent by weight, more preferably greater than about 98 percent by weight, and most preferably greater than about 99 percent by weight.

In another embodiment, the optional organic solvent is present and comprises propylene glycol. In another embodiment, the optional organic solvent is present and is propylene glycol.

In another embodiment, the optional organic solvent is present and comprises glycerol. In another embodiment, the optional organic solvent is present and is glycerol.

The total amount of solvent (i.e., poly(ethylene glycol) plus the optional organic solvent) typically ranges from about 10 to about 98 wt % of the pharmaceutical composition.

In another embodiment, the total amount of solvent is from about 20 to about 98 wt % of the pharmaceutical composition.

In another embodiment, the total amount of solvent is from about 25 to about 90 wt % of the pharmaceutical composition.

In another embodiment, the total amount of solvent is from about 35 to about 95 wt % of the pharmaceutical composition.

In another embodiment, the total amount of solvent is from about 45 to about 90 wt % of the pharmaceutical composition.

In another embodiment, the total amount of solvent is from about 50 to about 95 wt % of the pharmaceutical composition.

In another embodiment, the total amount of solvent is from about 60 to about 90 wt % of the pharmaceutical composition.

In another embodiment, the total amount of solvent is from about 55 to about 95 wt % of the pharmaceutical composition.

In another embodiment, the total amount of solvent is from about 70 to about 98 wt % of the pharmaceutical composition.

The amount of the optional organic solvent, when present, can be up to about 50 wt % of the total amount of solvent.

In one embodiment, the pharmaceutical composition contains substantially no optional organic solvent.

In another embodiment, the amount of the optional organic solvent is up to about 40 wt % of the total amount of solvent.

In another embodiment, the amount of the optional organic solvent is up to about 30 wt % of the total amount of solvent.

In another embodiment, the amount of the optional organic solvent is up to about 20 wt % of the total amount of solvent.

In another embodiment, the amount of the optional organic solvent is up to about 10 wt % of the total amount of solvent.

In another embodiment, the amount of the optional organic solvent is up to about 5 wt % of the total amount of solvent.

In another embodiment, the amount of the optional organic solvent is from about 5 wt % to about 40 wt % of the total amount of solvent.

In another embodiment, the amount of the optional organic solvent is from about 10 wt % to about 30 wt % of the total amount of solvent.

In another embodiment, the amount of the optional organic solvent is from about 5 wt % to about 25 wt % of the total amount of solvent.

In another embodiment, the amount of the optional organic solvent is from about 10 wt % to about 20 wt % of the total amount of solvent.

In one embodiment, the poly(ethylene glycol) has an average molecular weight of about 500 g/mol.

In another embodiment, the poly(ethylene glycol) has an average molecular weight of about 400 g/mol.

In another embodiment, the poly(ethylene glycol) has an average molecular weight of about 400 g/mol, glycerol is the organic solvent, and the poly(ethylene glycol) and glycerol are present in the pharmaceutical composition in a volume ratio of about 80:20.

In one embodiment, the pharmaceutical composition comprises poly(acrylic acid), glycerol, and poly(ethylene glycol).

In another embodiment, the pharmaceutical composition comprises a crosslinked poly(acrylic acid), glycerol, and poly(ethylene glycol) having an average molecular weight of about 400 g/mol.

In another embodiment, the pharmaceutical composition comprises from about 0.1 to about 2 wt % crosslinked poly(acrylic acid), from about 5 to about 30 wt % glycerol, and from about 60 to about 93 wt % poly(ethylene glycol) having an average molecular weight of about 400 g/mol.

In another embodiment, the pharmaceutical composition comprises from about 0.1 to about 1 wt % crosslinked poly(acrylic acid), from about 5 to about 30 wt % glycerol, and from about 60 to about 93 wt % poly(ethylene glycol) having an average molecular weight of about 400 g/mol.

In another embodiment, the pharmaceutical composition comprises about 0.5 wt % crosslinked poly(acrylic acid), from about 19 to about 20 wt % glycerol, and from about 73 to about 79 wt % poly(ethylene glycol) having an average molecular weight of about 400 g/mol.

Any pharmaceutically active agent can be used in the pharmaceutical compositions according to the invention. However, it is preferred that the pharmaceutically active agent not have more than one amino group. Without wishing to be bound by theory, it is believed that pharmaceutically active agents having more than one amino group can cause additional crosslinking with the poly(acrylic acid) polymer, resulting in a gel too viscous for the desired application.

The pharmaceutical composition of the invention can be prepared by simply adding the pharmaceutically active agent(s) to the poly(ethylene glycol) and the optional organic solvent, if present (typically about 90% of the total amount of the solvent desired in the final pharmaceutical composition), and agitating the resulting mixture until the pharmaceutically active agent(s) dissolve(s). One or more optional additive components can simultaneously and/or sequentially be added and the mixture agitated until additive component(s) dissolve(s). The poly(acrylic acid) polymer can then be added followed by additional solvent, to provide the desired concentration of the pharmaceutically active agent(s) in the pharmaceutical composition. Optionally, the solvent is warmed to a temperature of about 40° C. before the poly(acrylic acid) polymer is added. Once all the desired components are added, the resulting solution can then be homogenized, e.g., for about 1 to about 10 minutes, to form a uniform pharmaceutical composition. Without being bound to theory, it is believed that longer homogenization time and higher homogenization speeds result in a pharmaceutical composition having reduced viscosity. Following homogenization, the composition can be allowed to sit undisturbed until a gel is formed. One skilled in the art, however, will readily recognize that modifications to the above-described method for preparing the pharmaceutical compositions of the invention are possible, for example the order of adding the components to the solvent(s) can be changed.

7.4 Pharmaceutically Active Agents

In one embodiment, the pharmaceutically active agent is present as a pharmaceutically acceptable salt of the pharmaceutically active agent.

In another embodiment, the pharmaceutically active agent is a zwitterion.

In another embodiment, the pharmaceutically active agent is a basic compound.

In another embodiment, the pharmaceutically active agent is an acidic compound.

In another embodiment, the pharmaceutically active agent is a neutral compound.

The amount of pharmaceutically active agent in the pharmaceutical compositions typically ranges from about 0.01 to about 5 wt % of the pharmaceutical composition.

In another embodiment, the amount of pharmaceutically active agent in the pharmaceutical composition is from about 0.05 to about 5 wt % of the pharmaceutical composition.

In another embodiment, the amount of pharmaceutically active agent in the pharmaceutical composition is from about 0.1 to about 3 wt % of the pharmaceutical composition.

In another embodiment, the amount of pharmaceutically active agent in the pharmaceutical composition is from about 0.3 to about 2 wt % of the pharmaceutical composition.

In another embodiment, the amount of pharmaceutically active agent in the pharmaceutical composition is from about 0.5 to about 4 wt % of the pharmaceutical composition.

In one embodiment, the amount of pharmaceutically active agent in the pharmaceutical composition is from about 1 to about 5 wt % of the pharmaceutical composition.

In one embodiment, the amount of pharmaceutically active agent in the pharmaceutical composition is from about 0.2 to about 2.5 wt % of the pharmaceutical composition.

In another embodiment, the amount of pharmaceutically active agent in the pharmaceutical composition is from about 0.05 to about 1.5 wt % of the pharmaceutical composition.

In another embodiment, the amount of pharmaceutically active agent in the pharmaceutical composition is from about 0.01 to about 1 wt % of the pharmaceutical composition.

One of ordinary skill in the art will recognize, however, that the amount of pharmaceutically active agent in the pharmaceutical compositions according to the invention can vary widely depending on the pharmaceutically active agent and any other components present in the pharmaceutical composition.

Examples of active agents useful as the active agent component of the composition according to the invention include, but are not limited to, α-adrenergic agonists, β-adrenergic agonists, α-adrenergic blockers, β-adrenergic blockers, aldose reductase inhibitors, anabolics, analgesics (narcotic and non-narcotic), androgens, anesthetics, anorexics, anthelmintics (e.g., cestode, nematode, onchocerca, schistosoma, and the like), anti-allergics, anti-ameboics, anti-androgens, anti-anginals, anti-arrhythmics, anti-arteriosclerotics, antiarthritics, antibiotics and other antibacterials, anti-cholinergics, anti-convulsants, anti-depressants, anti-diabetics agents, anti-diarrheals, anti-diuretics, anti-estrogens, antifungals, anti-yeast agents, anti-glaucomas, anti-gonadotropins, anti-gout agents, anti-histaminics, anti-hyperlipoproteinemics, anti-hypertensives, anti-hyperthyroid agents, anti-hypertrophy agents, anti-hypotensives, anti-hypothyroid agents, antiinflammatories, anti-malarials, antimicrobials, anti-migraine agents, anti-nausea agents, anti-neoplastics, antioxidants, antiparasitic agents, anti-parkinsonian agents, anti-pheochromocytoma agents, anti-pneumocytis agents, antiproliferative agents, anti-protozoals (e.g., leishmania, trichomonas, trypansoma, and the like), anti-pruritic agents, anti-psoratic agents, anti-psychotic agents, anti-pyretics, anti-rheumatics, anti ricketts agents, anti-seborrheic agents, antiseptics, anti-spasmodic agents, anti-thrombotic agents, antitussives, anti-ulcer agents, anti-urolithic agents, antivenins, antivirals, anxiolytics, benzodiazepine antagonists, bronchodilators, calcium channel blockers, calcium regulators, cardiotonics, chelating agents, chemotherapeutics, cholecystokinin antagonists, cholelitholytic agents, choleretics, cholinergics, cholinesterase inhibitors, cholinesterase reactivators, central nervous system stimulants and agents, decongestants, diuretics, dopamine receptor agonists, drugs for treating or preventing pain, ectoparasiticides, enzymes, enzyme inducers, estrogens, gastric secretion inhibitors, glucocorticoids, gonad-stimulating principles, gonadotropic hormones, growth hormones, growth hormone releasing factors, growth stimulants, hemolytics, heparin agonists, hepatoprotectants, hypnotics, immune system boosters, immunomodulators, immunosuppressants, lactation stimulating hormones, LH-RH stimulating agonists, lipotropics, lupus erythmatosus suppressants, mineral corticoids, miotics, monoamine oxidase inhibitors, mucolytics, muscle relaxants, narcotic antagonists, neuroprotectives, neotropics, ovarian hormones, oxytocics, pepsin inhibitors, peristaltic stimulators, progestrogens, prolactin inhibitors, protoglandins, prostoglandin analogs, protease inhibitors, respiratory stimulants, sclerosing agents, sedatives, steroids, thrombolytics, thyrotropic hormones, transdermal penetration enhancers, uricosurics, vasoconstrictors, vasodilators (e.g., cerebral, coronary, peropheral, and the like), vasoprotectants, vitamins, vitamin source extracts, vulneraries (including, but not limited to, those listed in U.S. Pat. No. 5,719,197, the entire disclosure of which is incorporated herein by reference), and combinations thereof. Other additionally or alternately acceptable pharmaceutically active agents can be found, e.g., in U.S. Pat. No. 6,221,383, the entire disclosure of which is incorporated herein by reference.

In one embodiment, the pharmaceutically active agent comprises an antibacterial agent.

In another embodiment, the pharmaceutically active agent comprises an antifungal agent.

In another embodiment, the pharmaceutically active agent comprises an antiparasitic agent.

In another embodiment, the pharmaceutically active agent comprises an antiviral agent.

In another embodiment, the pharmaceutically active agent comprises an anti-yeast agent.

In another embodiment, the pharmaceutically active agent comprises a steroid.

In another embodiment, the pharmaceutically active agent comprises an antiinflammatory agent.

Examples of useful antibacterial agents include, but are not limited to, β-lactam antibiotics such as penicillins, amoxicillin, ampicillin, and cephalosporins; macrolide antibiotics such as oleandomycin and erythromycin; tetracyclines such as tetracycline, oxytetracycline, and chlortetracycline; procaine penicillin G; quinolones such as enrofloxacin, nalidixic acid and norfloxacin; sulfonamides; chloramphenicol; florfenicol; thiamphenicol, aminoglycosides such as tobramycin, streptomycin, kanamycin, and gentamycins; nucleoside antibiotics such as polyoxin B; actinorhodine; bacitracin; candicidin A; ceftiofor; clindamycin; cycloheximide; cycloserine; fosfomycin; griseofulvin; metronidazole; monensin; novobiocin; rifampin; streptothricin; tetranactin; tilmicosin; tylosin; actinomycin D; adriamycin; bleomycin B2; glycolipids such as moenomycin A; mitomycin C; nojirimycin; valinomycin; and vancomycin; (See, e.g., Bradford P. Smith, *Large Animal Internal Medicine,* 2nd edn., Mosby, St. Louis, 1996, p. 644, and S. Birchard and R. Sherding, *Saunders Manual of Small Animal Practice*, W.B. Saunders Company, Philadelphia, 1994, p. 739).

Examples of useful antifungal agents include, but are not limited to amphotericin B, clotrimazole, ketaconazole, miconazole, 5-fluorocytosine, enilconazole, itraconazole, thiabendazole, and iodides (See, e.g., Bradford P. Smith, *Large Animal Internal Medicine,* 2nd edn., Mosby, St. Louis, 1996, p. 576, and S. Birchard and R. Sherding, *Saunders Manual of Small Animal Practice*, W.B. Saunders Company, Philadelphia, 1994, p. 576).

Examples of useful antiviral agents include, but are not limited to, interferon (See, e.g., Bradford P. Smith, *Large Animal Internal Medicine,* 2nd edn., Mosby, St. Louis, 1996, p. 646).

Examples of useful anti-yeast agents include, but are not limited to, aminoglycosides such as tobramycin, streptomycin, kanamycin, and gentamicin.

Examples of useful antiparasitic agents include, but are not limited to nitazoxanide (NTA); benzimidazoles, such as thiabendazole, fenbendazole, mebendazole, oxfendazole, oxibendazole, albendazole, parbendazole, and febantel; tetrahydropyridines such as morantel tartrate/pyrantel pamoate; levamisole, organophosphates such as haloxon, coumaphos, trichlorfon, and dichlorvos; piperazine salts; ivermectin; and phenothiazine (See, e.g., Bradford P. Smith, *Large Animal Internal Medicine,* 2nd edn., Mosby, St. Louis, 1996, p. 1688).

Examples of useful antiinflammatory agents include, but are not limited to, steroids such as betamethasone; corticosteroids such as dexamethasone; antihistamines; and non-steroidal antiinflammatory drugs such as diclofenac, aspirin, flunixin meglumine, phenylbutazone, and ibuprofin (See, e.g., Bradford P. Smith, *Large Animal Internal Medicine,* 2nd edn., Mosby, St. Louis, 1996, p. 645).

In one embodiment, there can be multiple pharmaceutically active agents in a single pharmaceutical composition.

In another embodiment, the pharmaceutically active agent comprises the combination of an antibacterial agent, an antifungal agent, and a steroid.

Effective amounts of these pharmaceutically active agents are known to those skilled in the art. It is well within the skilled artisan's purview to determine each pharmaceutically active agent's optimal effective-amount range.

In one embodiment of the invention, where multiple pharmaceutically active agents are administered to an animal, the effective amount each pharmaceutically active agent is less than its effective amount would be were the other pharmaceutically active agent(s) not administered. In this case, without being bound by theory, it is believed that multiple pharmaceutically active agents act synergistically to treat or prevent a condition (e.g., a bacterial infection).

In one embodiment, the pharmaceutically active agent comprises Tobramycin.

In another embodiment, the pharmaceutically active agent comprises Tobramycin decanoic fatty acid salt.

In another embodiment, the pharmaceutically active agent comprises Tobramycin oleic fatty acid salt.

In another embodiment, the pharmaceutically active agent comprises Tobramycin acetic acid salt.

In another embodiment, the pharmaceutically active agent comprises Terbinafine.

In another embodiment, the pharmaceutically active agent comprises Terbinafine decanoic fatty acid salt.

In another embodiment, the pharmaceutically active agent comprises Terbinafine oleic fatty acid salt.

In another embodiment, the pharmaceutically active agent comprises Terbinafine acetic acid salt.

In another embodiment, the pharmaceutically active agent comprises Betamethasone.

In another embodiment, the pharmaceutically active agent comprises Betamethasone acetate.

In another embodiment, the pharmaceutically active agent comprises Florfenicol.

In another embodiment, the pharmaceutically active agent comprises Thiamphenicol.

In another embodiment, the pharmaceutically active agent comprises Chloramphenicol.

In another embodiment, the pharmaceutically active agent comprises Gentamicin.

In another embodiment, the pharmaceutically active agent comprises Clotrimazole.

In another embodiment, the pharmaceutically active agent comprises Tilmicosin.

In another embodiment, the pharmaceutically active agent comprises a Tetracycline compound.

In another embodiment, the pharmaceutically active agent comprises Ketoconazole.

In another embodiment, the pharmaceutically active agent comprises Diclofenac.

In another embodiment, the pharmaceutically active agent comprises Flunixin.

In another embodiment, the pharmaceutically active agent comprises Carprofen.

In another embodiment, the pharmaceutically active agent comprises a Cephalosporin.

In another embodiment, the pharmaceutically active agent comprises a combination of Tobramycin or a pharmaceutically acceptable salt thereof, Terbinafine or a pharmaceutically acceptable salt thereof, and Betamethasone or a pharmaceutically acceptable ester thereof.

In another embodiment, the pharmaceutically active agent comprises a combination of Tobramycin decanoic fatty acid salt, Terbinafine decanoic fatty acid salt, and Betamethasone or a pharmaceutically acceptable ester thereof.

In another embodiment, the pharmaceutically active agent comprises from about 0.5 to about 3 wt % of Tobramycin decanoic fatty acid salt, from about 0.5 to about 3 wt % of Terbinafine decanoic fatty acid salt, and from about 0.01 to about 0.5 wt % of Betamethasone or a pharmaceutically acceptable ester thereof.

In another embodiment, the pharmaceutically active agent comprises about 1 wt % of Tobramycin decanoic fatty acid salt, about 1 wt % of Terbinafine decanoic fatty acid salt, and about 0.1 wt % of Betamethasone or a pharmaceutically acceptable ester thereof.

In another embodiment, the pharmaceutically active agent comprises a combination of Florfenicol or a pharmaceutically acceptable ester thereof, Terbinafine or a pharmaceutically acceptable salt thereof, and Betamethasone or a pharmaceutically acceptable ester thereof.

In another embodiment, the pharmaceutically active agent comprises a combination of Florfenicol or a pharmaceutically acceptable ester thereof, Terbinafine oleic fatty acid salt, and Betamethasone or a pharmaceutically acceptable ester thereof.

In another embodiment, the pharmaceutically active agent comprises from about 0.5 to about 3 wt % of Florfenicol or a pharmaceutically acceptable ester thereof, from about 0.5 to about 3 wt % of Terbinafine oleic fatty acid salt, and from about 0.01 to about 0.5 wt % of Betamethasone or a pharmaceutically acceptable ester thereof.

In another embodiment, the pharmaceutically active agent comprises about 1 wt % of Florfenicol or a pharmaceutically acceptable ester thereof, about 1 wt % of Terbinafine oleic fatty acid salt, and about 0.1 wt % of Betamethasone or a pharmaceutically acceptable ester thereof.

In another embodiment, the pharmaceutically active agent comprises Gentamycin or a pharmaceutically acceptable salt thereof, Clotrimazole or a pharmaceutically acceptable salt thereof, and Betamethasone or a pharmaceutically acceptable ester thereof.

In another embodiment, the pharmaceutically active agent comprises from about 0.5 to about 3 wt % of Gentamycin or a pharmaceutically acceptable salt thereof, from about 0.5 to about 3 wt % of Clotrimazole or a pharmaceutically acceptable salt thereof, and from about 0.01 to about 0.5 wt % of Betamethasone or a pharmaceutically acceptable ester thereof.

In another embodiment, the pharmaceutically active agent comprises about 1 wt % of Gentamycin or a pharmaceutically acceptable salt thereof, about 1 wt % of Clotrimazole or a pharmaceutically acceptable salt thereof, and about 0.1 wt % of Betamethasone or a pharmaceutically acceptable ester thereof.

In one embodiment, the pharmaceutically active agent has an amine moiety and is present in the pharmaceutical composition of the invention as a fatty acid salt ("FAS") by converting the amine moiety to an ammonium cation whose counterion is a fatty acid moiety such as those described in International Publication No. WO 03/034988 A2, the entire disclosure of which is incorporated herein in its entirety.

Without being bound to theory, it is believed that a FAS of a pharmaceutically active agent provides additional sustained- or controlled-release of the pharmaceutically active agent (as reflected in more steady blood levels as a function of time). Without wishing to be bound by theory, it is believed that the additional sustained- or controlled-release of the pharmaceutically active agent obtained when using a FAS of a pharmaceutically active agent is because the FAS of a pharmaceutically active agent is less soluble in water than the pharmaceutically active agent itself or other non-fatty acid salt of the pharmaceutically active agent and, accordingly, is absorbed by the animal more slowly.

7.5 Optional Pharmaceutical Composition Additives

The present pharmaceutical compositions can optionally comprise a suitable amount of a pharmaceutically acceptable preservative, if desired, so as to provide additional protection against microbial growth.

Examples of preservatives useful in the pharmaceutical compositions of the invention include, but are not limited to, potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quarternary compounds such as benzalkonium chlorides (e.g., benzethonium chloride).

In one embodiment, any additional components added to the pharmaceutical compositions of the invention are designated as GRAS ("generally recognized as safe") by the FDA for use or consumption by animals.

In another embodiment, any additional components added to the pharmaceutical compositions of the invention are designated as GRAS by the FDA for use or consumption by humans.

In one embodiment, any additional components added to the pharmaceutical compositions of the invention are sterile when administered to an animal.

7.6 The Pharmaceutical Compositions

In one embodiment, the pharmaceutical composition has a viscosity of greater than about 1,000 cps at about 25° C.

In another embodiment, the pharmaceutical composition has a viscosity of greater than about 2,000 cps at about 25° C.

In another embodiment, the pharmaceutical composition has a viscosity of greater than about 5,000 cps at about 25° C.

In another embodiment, the pharmaceutical composition has a viscosity of greater than about 10,000 cps at about 25° C.

In another embodiment, the pharmaceutical composition has a viscosity of greater than about 15,000 cps at about 25° C.

In another embodiment, the pharmaceutical composition has a viscosity of greater than about 20,000 cps at about 25° C.

In another embodiment, the pharmaceutical composition has a viscosity of greater than about 25,000 cps at about 25° C.

Typically, the pharmaceutical composition has a viscosity of less than about 100,000 cps at about 25° C.

In one embodiment, the pharmaceutical composition has a viscosity of less than about 75,000 cps at about 25° C.

In another embodiment, the pharmaceutical composition has a viscosity that ranges from about 1,000 cps to about 100,000 cps at about 25° C.

In another embodiment, the pharmaceutical composition has a viscosity that ranges from about 2,000 cps to about 100,000 cps at about 25° C.

In another embodiment, the pharmaceutical composition has a viscosity that ranges from about 5,000 cps to about 100,000 cps at about 25° C.

In another embodiment, the pharmaceutical composition has a viscosity that ranges from about 10,000 cps to about 100,000 cps at about 25° C.

In another embodiment, the pharmaceutical composition has a viscosity that ranges from about 20,000 cps to about 100,000 cps at about 25° C.

In another embodiment, the pharmaceutical composition has a viscosity that ranges from about 25,000 cps to about 100,000 cps at about 25° C.

In another embodiment, the pharmaceutical composition has a viscosity that ranges from about 2,000 cps to about 75,000 cps at about 25° C.

In another embodiment, the pharmaceutical composition has a viscosity that ranges from about 5,000 cps to about 75,000 cps at about 25° C.

In another embodiment, the pharmaceutical composition has a viscosity that ranges from about 10,000 cps to about 75,000 cps at about 25° C.

In another embodiment, the pharmaceutical composition has a viscosity that ranges from about 20,000 cps to about 75,000 cps at about 25° C.

In another embodiment, the pharmaceutical composition has a viscosity that ranges from about 25,000 cps to about 75,000 cps at about 25° C.

In another embodiment, the pharmaceutical composition has a viscosity that ranges from about 1,000 cps to about 25,000 cps at about 25° C.

In another embodiment, the pharmaceutical composition has a viscosity that ranges from about 2,000 cps to about 25,000 cps at about 25° C.

In another embodiment, the pharmaceutical composition has a viscosity that ranges from about 5,000 cps to about 25,000 cps at about 25° C.

In another embodiment, the pharmaceutical composition has a viscosity that ranges from about 2,000 cps to about 18,000 cps at about 25° C.

In another embodiment, the pharmaceutical composition has a viscosity that ranges from about 5,000 cps to about 18,000 cps at about 25° C.

Viscosity is determined using a Brookfield DV-E viscometer (commercially available from Brookfield of Middleboro, Mass.)

In one embodiment, the pharmaceutical composition is substantially free of water. Pharmaceutical compositions that are substantially free of water are advantageous since they are not conducive to bacterial growth. Accordingly, it is typically not necessary to include a preservative in pharmaceutical compositions that are substantially free of water. However, in some embodiments, the non-aqueous pharmaceutical composition contains a preservative.

In one embodiment, the pharmaceutical composition comprises hydroxypropyl methyl cellulose, glycerol, glycerol formal, Tobramycin or a pharmaceutically acceptable salt thereof, Terbinafine or a pharmaceutically acceptable salt thereof, and Betamethasone or a pharmaceutically acceptable ester thereof.

In another embodiment, the pharmaceutical composition comprises hydroxypropyl methyl cellulose, glycerol, glycerol formal, Tobramycin decanoic fatty acid salt, Terbinafine decanoic fatty acid salt, and Betamethasone or a pharmaceutically acceptable ester thereof.

In another embodiment, the pharmaceutical composition comprises from about 0.2 to about 7 wt % hydroxypropyl methyl cellulose, from about 3 to about 20 wt % glycerol, from about 65 to about 86 wt % glycerol formal, from about 0.5 to about 3 wt % of Tobramycin decanoic fatty acid salt, from about 0.5 to about 3 wt % of Terbinafine decanoic fatty acid salt, and from about 0.01 to about 0.5 wt % of Betamethasone or a pharmaceutically acceptable ester thereof.

In another embodiment, the pharmaceutical composition comprises about 4 wt % hydroxypropyl methyl cellulose, from about 9 to about 10 wt % glycerol, from about 78 to about 85 wt % glycerol formal, about 1 wt % of Tobramycin decanoic fatty acid salt, about 1 wt % of Terbinafine decanoic fatty acid salt, and about 0.1 wt % of Betamethasone or a pharmaceutically acceptable ester thereof.

In another embodiment, the pharmaceutical composition comprises hydroxypropyl methyl cellulose, glycerol, glycerol formal, Tobramycin or a pharmaceutically acceptable salt thereof, Terbinafine or a pharmaceutically acceptable salt thereof, Betamethasone or a pharmaceutically acceptable salt thereof, and Benzethonium chloride.

In another embodiment, the pharmaceutical composition comprises hydroxypropyl methyl cellulose, glycerol, glycerol formal, Tobramycin decanoic fatty acid salt, Terbinafine decanoic fatty acid salt, Betamethasone or a pharmaceutically acceptable ester thereof, and Benzethonium chloride.

In another embodiment, the pharmaceutical composition comprises from about 0.2 to about 7 wt % hydroxypropyl methyl cellulose, from about 3 to about 20 wt % glycerol, from about 65 to about 86 wt % glycerol formal, from about 0.5 to about 3 wt % of Tobramycin decanoic fatty acid salt, from about 0.5 to about 3 wt % of Terbinafine decanoic fatty acid salt, from about 0.01 to about 0.5 wt % of Betamethasone or a pharmaceutically acceptable ester thereof, and from about 0.005 to about 0.1 wt % of Benzethonium chloride.

In another embodiment, the pharmaceutical composition comprises about 4 wt % hydroxypropyl methyl cellulose, from about 9 to about 10 wt % glycerol, from about 78 to about 85 wt % glycerol formal, about 1 wt % of Tobramycin decanoic fatty acid salt, about 1 wt % of Terbinafine decanoic fatty acid salt, about 0.1 wt % of Betamethasone or a pharmaceutically acceptable ester thereof, and about 0.02 wt % of Benzethonium chloride.

In one embodiment, the pharmaceutical composition comprises poly(acrylic acid), glycerol, poly(ethylene glycol), Florfenicol or a pharmaceutically acceptable ester thereof, Terbinafine or a pharmaceutically acceptable salt thereof, and Betamethasone or a pharmaceutically acceptable ester thereof.

In another embodiment, the pharmaceutical composition comprises a crosslinked poly(acrylic acid), glycerol, poly(ethylene glycol) having an average molecular weight of about 400 g/mol, Florfenicol or a pharmaceutically acceptable ester thereof, Terbinafine oleic fatty acid salt, and Betamethasone or a pharmaceutically acceptable ester thereof.

In another embodiment, the pharmaceutical composition comprises from about 0.1 to about 5 wt % crosslinked poly(acrylic acid), from about 5 to about 30 wt % glycerol, from about 60 to about 93 wt % poly(ethylene glycol) having an average molecular weight of about 400 g/mol, from about 0.5 to about 3 wt % of Florfenicol or a pharmaceutically acceptable ester thereof, from about 0.5 to about 3 wt % of Terbinafine oleic fatty acid salt, and from about 0.01 to about 0.5 wt % of Betamethasone or a pharmaceutically acceptable ester thereof.

In another embodiment, the pharmaceutical composition comprises about 0.5 wt % crosslinked poly(acrylic acid), from about 19 to about 20 wt % glycerol, from about 73 to about 79 wt % poly(ethylene glycol) having an average molecular weight of about 400 g/mol, about 1 wt % of Florfenicol or a pharmaceutically acceptable ester thereof, about 1 wt % of Terbinafine oleic fatty acid salt, and about 0.1 wt % of Betamethasone or a pharmaceutically acceptable ester thereof.

In one embodiment, the pharmaceutical composition comprises poly(acrylic acid), glycerol, poly(ethylene glycol), Florfenicol or a pharmaceutically acceptable ester thereof, Terbinafine or a pharmaceutically acceptable salt thereof, Betamethasone or a pharmaceutically acceptable ester thereof, and Benzethonium chloride.

In another embodiment, the pharmaceutical composition comprises a crosslinked poly(acrylic acid), glycerol, poly(ethylene glycol) having an average molecular weight of about 400 g/mol, Florfenicol or a pharmaceutically acceptable ester thereof, Terbinafine oleic fatty acid salt, Betamethasone or a pharmaceutically acceptable ester thereof, and Benzethonium chloride.

In another embodiment, the pharmaceutical composition comprises from about 0.1 to about 5 wt % crosslinked poly(acrylic acid), from about 5 to about 30 wt % glycerol, from about 60 to about 93 wt % poly(ethylene glycol) having an average molecular weight of about 400 g/mol, from about 0.5 to about 3 wt % of Florfenicol or a pharmaceutically acceptable ester thereof, from about 0.5 to about 3 wt % of Terbinafine oleic fatty acid salt, from about 0.01 to about 0.5 wt % of Betamethasone or a pharmaceutically acceptable ester thereof, and from about 0.005 to about 0.1 wt % of Benzethonium chloride.

In another embodiment, the pharmaceutical composition comprises about 0.5 wt % crosslinked poly(acrylic acid), from about 19 to about 20 wt % glycerol, from about 73 to about 79 wt % poly(ethylene glycol) having an average molecular weight of about 400 g/mol, about 1 wt % of Florfenicol or a pharmaceutically acceptable ester thereof, about 1 wt % of Terbinafine oleic fatty acid salt, about 0.1 wt % of Betamethasone or a pharmaceutically acceptable ester thereof, and about 0.02 wt % of Benzethonium chloride.

In one embodiment, the pharmaceutical composition comprises hydroxypropyl methyl cellulose, glycerol, glycerol formal, Gentamicin or a pharmaceutically acceptable salt thereof, Clotrimazole or a pharmaceutically acceptable salt thereof, and Betamethasone or a pharmaceutically acceptable ester thereof.

In another embodiment, the pharmaceutical composition comprises hydroxypropyl methyl cellulose, glycerol, glycerol formal, Gentamicin decanoic fatty acid salt, Clotrimazole decanoic fatty acid salt, and Betamethasone or a pharmaceutically acceptable ester thereof.

In another embodiment, the pharmaceutical composition comprises from about 0.2 to about 7 wt % hydroxypropyl methyl cellulose, from about 3 to about 20 wt % glycerol, from about 65 to about 86 wt % glycerol formal, from about 0.5 to about 3 wt % of Gentamicin decanoic fatty acid salt, from about 0.5 to about 3 wt % of Clotrimazole decanoic fatty acid salt, and from about 0.01 to about 0.5 wt % of Betamethasone or a pharmaceutically acceptable ester thereof.

In another embodiment, the pharmaceutical composition comprises about 4 wt % hydroxypropyl methyl cellulose, from about 9 to about 10 wt % glycerol, from about 78 to about 85 wt % glycerol formal, about 1 wt % of Gentamicin decanoic fatty acid salt, about 1 wt % of Clotrimazole decanoic fatty acid salt, and about 0.1 wt % of Betamethasone or a pharmaceutically acceptable ester thereof.

In another embodiment, the pharmaceutical composition comprises hydroxypropyl methyl cellulose, glycerol, glycerol formal, Gentamicin or a pharmaceutically acceptable salt thereof, Clotrimazole or a pharmaceutically acceptable salt thereof, Betamethasone or a pharmaceutically acceptable salt thereof, and Benzethonium chloride.

In another embodiment, the pharmaceutical composition comprises hydroxypropyl methyl cellulose, glycerol, glycerol formal, Gentamicin decanoic fatty acid salt, Clotrimazole decanoic fatty acid salt, Betamethasone or a pharmaceutically acceptable ester thereof, and Benzethonium chloride.

In another embodiment, the pharmaceutical composition comprises from about 0.2 to about 7 wt % hydroxypropyl methyl cellulose, from about 3 to about 20 wt % glycerol, from about 65 to about 86 wt % glycerol formal, from about 0.5 to about 3 wt % of Gentamicin decanoic fatty acid salt, from about 0.5 to about 3 wt % of Clotrimazole decanoic fatty acid salt, from about 0.01 to about 0.5 wt % of Betamethasone or a pharmaceutically acceptable ester thereof, and from about 0.005 to about 0.1 wt % of Benzethonium chloride.

In another embodiment, the pharmaceutical composition comprises about 4 wt % hydroxypropyl methyl cellulose, from about 9 to about 10 wt % glycerol, from about 78 to about 85 wt % glycerol formal, about 1 wt % of Gentamicin decanoic fatty acid salt, about 1 wt % of Clotrimazole decanoic fatty acid salt, about 0.1 wt % of Betamethasone or a pharmaceutically acceptable ester thereof, and about 0.02 wt % of Benzethonium chloride.

7.7 Methods of Treating or Preventing a Condition in an Animal

In one embodiment, the method of treating or preventing a condition in an animal comprises administering to the animal in need thereof a therapeutically effective amount of a pharmaceutically active agent by otically applying a pharmaceutical composition of the invention.

In one embodiment, the method of treating or preventing a condition in an animal comprises administering to the animal in need thereof a therapeutically effective amount of a pharmaceutically active agent by ophthalmically applying a pharmaceutical composition of the invention.

In one embodiment, the method of treating or preventing a condition in an animal comprises administering to the animal in need thereof a therapeutically effective amount of a pharmaceutically active agent by topically applying a pharmaceutical composition of the invention.

The pharmaceutical compositions of the invention can also be administered orally. To administer the pharmaceutical compositions orally, the pharmaceutical composition can, for example, be encapsulated in a capsule, such as a hard gelatin capsule or a soft gelatin capsule, and the capsule orally administered to the animal. Suitable capsules for use in the invention are Shionogi Qualicaps (commercially available from and Shionogi & Co., Ltd of Osaka, Japan). Oral dosage forms can be designed to release the pharmaceutically active compound in the stomach immediately or almost immediately or to provide sustained release of the pharmaceutically active compound in the stomach. The oral dosage forms can also be designed to release the pharmaceutically active compound in the intestines immediately or almost immediately or to provide sustained release of the pharmaceutically active compound in the intestines. To delay the release of the pharmaceutically active compound until the dosage form reaches the intestines, the capsule is coated with an enteric coating. Typically, the enteric coating is a pH sensitive polymer such as Eudragit® L-100 (commercially available from DeGussa AG of Frankfurt, Germany). The rate of release of the pharmaceutically active compound is varied by varying, for example, the amount of polymer in the pharmaceutical composition, the degree of polymer cross-linking, and the solvent in the pharmaceutical composition.

The pharmaceutical compositions of the invention are viscous compositions. Viscous compositions containing drugs have advantages over less viscous (thinner) liquid formulations for treating or preventing conditions in animals. For example, in topical applications, otic applications, and ophthalmic applications, especially in veterinary uses, thinner liquid formulations are easily be washed or swept away from a target area of delivery than formulations that are more viscous (thicker). For treating conditions such as microbial infections, particularly in non-human animals, the advantages of thicker pharmaceutical compositions include maintaining the pharmaceutically active agent, like an antibiotic, in the target area for longer periods of time.

The pharmaceutical compositions of the invention are particularly useful in veterinary medicine, especially for otic applications. For example, when treating or preventing otic microbial infections in small animals, such as cats and dogs, the pharmaceutical composition is typically administered in an amount of about 0.5 mL per ear. Larger amounts, however, can be administered for larger animals.

The pharmaceutical compositions of the invention are advantageous in veterinary medicine, especially for otic application, compared to commercially available pharmaceutical compositions. For example, when treating or preventing otic microbial infections in animals using commercially available pharmaceutical compositions the animal typically shakes its head and dislodges the composition from the target infected area (and often out of the ear entirely). This occurs readily with commercially available antibiotic compositions since they have lower viscosity. However, the pharmaceutical compositions of the invention, having a higher viscosity, are not as easily dislodged, thus rendering them more effective in delivering the pharmaceutically active agent to the target infected area and remaining present for extended periods at the infected area to provide controlled- or sustained-release of the pharmaceutically active agent.

Advantageously, the pharmaceutical compositions of the invention need to be applied less frequently than commercially available pharmaceutical compositions. Often only two doses or a single dose of the pharmaceutical compositions of the invention are effective at treating or preventing otic microbial infections in animals. In contrast, commercially available pharmaceutical compositions typically require many more doses. For example, OTOMAX® (commercially available from Schering-Plough Animal Health of Union, N.J.) requires 2 doses per day for 7 days.

Further, the pharmaceutical compositions of the invention are typically more lipophilic than aqueous or semi-aqueous formulations. Without being bound by theory, it is believed that the increased lipophilicity of the pharmaceutical compositions of the invention renders them more effective than aqueous or semi-aqueous formulations, particularly for treating or preventing ear infections in an animal, because the pharmaceutical compositions of the invention are more compatible with the highly lipophilic environment of the animal's ear.

The pharmaceutical compositions of the invention also adhere well to the skin and, accordingly, are useful for topical application.

The pharmaceutical compositions of the invention can provide controlled- or sustained-release of the pharmaceutically active agent in a effective amount for up to about 15 days and even longer.

In one embodiment, the pharmaceutical compositions according to the invention provide controlled- or sustained-release of the pharmaceutically active agent in a pharmaceutically effective amount for at least about 4 to about 15 days.

In another embodiment, the pharmaceutical compositions according to the invention provide controlled- or sustained-release of the pharmaceutically active agent in a pharmaceutically effective amount for at least about 4 to about 10 days.

In another embodiment, the pharmaceutical compositions according to the invention provide controlled- or sustained-release of the pharmaceutically active agent in a pharmaceutically effective amount for at least about 1 week.

In one embodiment, the animal is a non-human animal.

In another embodiment, the animal is a human.

In another embodiment, the animal is a cat.

In another embodiment, the animal is a dog.

In another embodiment, the animal is a cow.

In another embodiment, the animal is a pig.

In another embodiment, the animal is a sheep.

In another embodiment, the animal is a horse.

In a preferred embodiment, the pharmaceutical compositions according to the invention, by providing controlled- or sustained-release of the pharmaceutically active agent, have reduced toxicity, particularly in small animals such as cats and dogs. Accordingly, the pharmaceutical compositions according to the invention have a better therapeutic profile than conventional immediate release formulations. Methods that involve administering a pharmaceutically active agent to an animal by topically, otically, or ophthalmically applying a pharmaceutical composition of the invention permit pharmaceutically active agents to be administered to animals that could potentially (if administered in presently available dosage forms) result in toxicity and even death of the animal being treated. By advantageously providing controlled- or sustained-release of the pharmaceutically active agents, the pharmaceutical composition of the invention can be administered less frequently and therefore also be easier to administer, more convenient, and more cost effective than conventional modes of administering pharmaceutically active agents.

The amount of the pharmaceutically active agent(s) that is(are) effective in treating or preventing a condition, e.g., a bacterial infection, can be determined by standard clinical techniques. In addition, in vitro or in vivo assays can optionally be employed to help identify optimal dosage ranges. The precise dose to be employed will also depend on the route of administration, the seriousness of the condition, and the animal being treated and can be decided according to the judgment of a practitioner and/or each animal's circumstances. Suitable effective dosage amounts, however, can typically range from about 0.1 mg/kg of body weight to about 100 mg/kg of body weight, preferably from about 1 mg/kg of body weight to about 50 mg/kg of body weight, more preferably from about 2 mg/kg of body weight to about 30 mg/kg of body weight, for example from about 5 mg/kg of body weight to about 100 mg/kg of body weight. The effective dosage amounts described herein refer to total amounts of all pharmaceutically active agents administered; that is, if more than one pharmaceutically active agent is administered, the effective dosage amounts correspond to the total amount administered.

Typically, topical compositions are applied from about 1 time each day to about 1 time each week until the condition is abated.

In one embodiment, the topical compositions are applied once each day until the condition is abated.

In another embodiment, the topical compositions are applied once each week until the condition is abated.

In another embodiment, the topical applications are applied for about 4 weeks.

In another embodiment, the topical applications are applied for about 3 weeks.

In another embodiment, the topical applications are applied for about 2 weeks.

In another embodiment, the topical applications are applied for about 1 week.

In one embodiment, an effective dosage amount is administered about every 7 days until the condition is abated.

In another embodiment, an effective dosage amount is administered about every 7 days for about 4 weeks.

In another embodiment, an effective dosage amount is administered about every 7 days for about 2 weeks.

In another embodiment, a single effective dosage amount is administered.

In another embodiment, 2 effective dosage amount are administered about 24 hours apart.

In another embodiment, 2 effective dosage amount are administered about 48 hours apart.

In another embodiment, an effective dosage amount is administered about every 24 hours until the condition is abated.

In another embodiment, an effective dosage amount is administered about every 12 hours until the condition is abated.

In another embodiment, an effective dosage amount is administered about every 24 hours for about 4 weeks.

In another embodiment, an effective dosage amount is administered about every 12 hours for about 4 weeks.

In another embodiment, an effective dosage amount is administered about every 24 hours for about 2 weeks.

In another embodiment, an effective dosage amount is administered about every 12 hours for about 2 weeks.

In another embodiment, an effective dosage amount is administered about every 24 hours for about 1 week.

In another embodiment, an effective dosage amount is administered about every 12 hours for about 1 week.

In another embodiment, an effective dosage amount is administered about every 7 days for about 2 weeks.

In another embodiment, an effective dosage amount is administered daily until the condition is abated. The total dose may optionally be divided into daily doses and/or into about 2 to about 4 individual doses.

In one embodiment, the condition is a bacterial infection.

Representative bacterial infections that can be treated using the pharmaceutical compositions of the invention include, but are not limited to, bacterial infections caused by bacteria of the genus *Pasteurella, Haemophilus, Fusobacterium, Moraxella, Bacteroides, Aeromonas, Escherichia, Enterobacter, Klebsiella, Salmonella, Shigella, Serratia, Ureaplasma, Chlamydia, Actinobacillus, Streptococcus, Edwardsiella, Staphylococcus, Enterococcus, Bordetella, Proteus, Mycoplasma,* or *Mannheimia.*

Representative bacterial infections that can be treated using the pharmaceutically active agents of the invention include, but are not limited to, bacterial infections caused by *Pasteurella haemolytica, Pasteurella multocida, Pasteurella haemolytica, Haemophilus somnus, Actinobacillus pleuropneumoniae, Actinomyces pyogenes, Pseudomonas aeruginosa, Klebsiella Pneumonia, Escherichia Faecalis, Escherichia Coli, Staphylococcus Aureaus, Streptococcus Pyogenes, Bacillus Subtilis, Streptococcus* spp., *Staphylococcus* spp., *Moraxella* spp., *Salmonella* spp., *Bacteroides* spp., *Peptococcus indolicus, Fusobacterium* spp., *Mycoplasma bovis, Mycoplasma dispar, Ureaplasma* spp., *Chlamydia* spp., *Mycoplasma mycoides, Mycoplasma ovipneumonia, Haemophilus influenzae, Klebsiella salmonella, Shigella, Proteus Enterobacter, Serratia*, and *Bordetella bronchoseptica*.

Without being bound by theory, it is believed that the presence of a non-aqueous gel surrounding or encapsulating the pharmaceutically active agent(s) allows for higher loading than that attainable in aqueous gels (where the maximum loading is believed to be about 0.3 percent by weight of the aqueous pharmaceutical composition) or through the use of liposomal formulations (where the maximum loading is believed to be about 1 percent by weight of the liposome-containing composition). Indeed, a pharmaceutical composition containing uniformly dispersed pharmaceutically active agents has been formulated to contain at least as much as about 5 percent by weight of the pharmaceutical compositions of the invention.

7.8 Kits

The invention encompasses kits that can simplify the administration of a pharmaceutically active agent to an animal. A typical kit of the invention comprises a unit dosage form of a pharmaceutical composition according to the invention. In one embodiment, the unit dosage form is a container (such as a vial, a pouch, a tube, a syringe, or the like), which can advantageously be sterile, containing a pharmaceutical composition of the invention. The kit can further comprise a label or printed instructions instructing the use of the pharmaceutically active agent to treat or prevent a condition. In another embodiment, the kit comprises a unit dosage form of a pharmaceutical composition of the invention and a dropper, syringe, or other applicator for administering the pharmaceutical composition. Typically, the components of the kit, for example, the unit dosage form and instructions, are contained within a suitable packaging material.

8. EXAMPLES

The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

Example 8.1

Polymer-Solvent Pharmaceutical Composition of the Invention

A mixture of about 63 grams glycerol and about 523.3 grams of stabilized glycerol formal was added to an empty flask. To the resulting mixture was added about 5 grams of Tobramycin, about 5 grams of Terbinafine, about 12.7 grams of decanoic acid, about 0.5 grams of Betamethasone acetate, and about 0.1 grams of Benzethonium chloride preservative with stirring. The resulting solution was stirred at about 40° C. to provide a clear solution. About 20 grams of HPMC (hydroxypropyl methyl cellulose) was then added to the clear solution, and the resulting solution was homogenized at about 3000 rpm with an Omni International model GLH Homogenizer (commercially available from Omni International of Marietta, Ga.) for about 3 minutes. The homogenized solution was allowed to sit undisturbed, in the dark, at a temperature of about 20-25° C. for about 12 hours. The resulting gel contained about 1 wt % Tobramycin as a decanoic acid salt, about 1 wt % Terbinafine as a decanoic acid salt, about 0.1 wt % Betamethasone acetate, and about 0.02 wt % Benzethonium chloride, and exhibited a viscosity of about 8,020 cps at 25° C.

Example 8.2

Polymer-Solvent Pharmaceutical Composition of the Invention

About 63 grams glycerol, about 5 grams of Tobramycin, about 3.75 grams of Terbinafine, about 3.2 grams of oleic acid, about 3.9 grams of decanoic acid, about 2 grams of acetic acid, about 0.5 grams of Betamethasone acetate, and about 0.1 grams of Benzethonium chloride preservative were combined in a flask with stirring. Stabilized glycerol formal was added to provide a total volume of about 500 mL. The resulting solution was then sonicated for about 10 minutes at a temperature of about 40° C. to provide a clear solution. The clear solution was then cooled to a temperature of about 20-25° C. The final weight of the about 500 mL solution was about 605 grams. The solution was then transferred to a 1 L beaker and equilibrated in a water bath at about 40° C. About 20 grams of HPMC (hydroxypropyl methyl cellulose) was then added to the clear solution, which was then homogenized at about 3000 rpm with an Omni International model GLH Homogenizer (commercially available from Omni International of Marietta, Ga.) for about 3 to about 5 minutes. The resulting homogenized solution was left undisturbed at about 40° C. for about 5 minutes, sonicated at about 40° C. for about 5 minutes to remove all visible bubbles from the solution, and allowed to sit undisturbed, in the dark, at a temperature of about 20-25° C. for about 12 hours to provide a gel. The resulting gel contained about 1 wt % Tobramycin as a mixture of decanoic acid, oleic acid, and acetic acid salts; about 1 wt % Terbinafine as a mixture of decanoic acid, oleic acid, and acetic acid salts; about 0.1 wt % Betamethasone acetate; and about 0.02 wt % Benzethonium chloride; and exhibited a viscosity of about 4,188 cps at 25° C.

Example 8.3

Polymer-Solvent Pharmaceutical Composition of the Invention

About 126 grams glycerol, about 5 grams of Florfenicol, about 5 grams of Terbinafine, about 6.5 grams of oleic acid, about 0.5 grams of Betamethasone acetate, and about 0.1 grams of Benzethonium chloride preservative were combined in a flask. About 430 grams of polyethylene glycol 400 (PEG 400) was added to the flask and the resulting solution was stirred at about 43° C. for about 45 minutes and then sonicated for about 5 minutes to provide a clear solution. The clear solution was then equilibrated in a water bath at about 40° C., and about 2.5 grams of CARBOMER™ 941 (crosslinked poly(acrylic acid) polymer, commercially available from Noveon, Inc., of Cleveland, Ohio) was added to the solution. The solution was then homogenized at about 3000 rpm using a Omni International model GLH Homogenizer (commercially available from Omni International of Marietta, Ga.) for about 5 minutes and then sonicated for about 5 minutes to remove all visible bubbles from the solution. The solution was allowed to sit undisturbed, at a temperature of about 20-25° C. for about 12 hours to provide a clear gel. The resulting gel contained about 1 wt % Florfenicol, about 1 wt % Terbinafine as an oleic acid salt, about 0.1 wt % Betamethasone acetate, and about 0.02 wt % Benzethonium chloride, and exhibited a viscosity of about 2,002 cps at 25° C.

Example 8.4

Polymer-Solvent Pharmaceutical Composition of the Invention

About 50.4 grams of glycerol were added to a first flask and sufficient ethyl lactate added to provide a volume of about 140 mL. The resultant mixture of solvents was stirred and heated to about 40° C. About 2.0 grams of Tobramycin and about 3.8 g of decanoic acid were added to the mixture of solvents and the resultant solution stirred until clear.

In a second flask was added about 2.0 grams of Terbinafine and about 2.88 mL of oleic acid and the resulting mixture heated to about 40° C. To the resultant mixture was added sufficient ethyl acetate to provide a volume of about 60 mL. To the resultant solution was added about 200 mg of Betamethasone acetate and about 40 mg of Benzethonium chloride, and the solution was stirred at about 40° C. until clear.

The contents of the first flask and the contents of the second flask were then combined and stirred at a temperature of about 40° C., and about 7.0 g of HPMC was added to the resulting solution with stirring. The resulting solution was then allowed to sit undisturbed at a temperature of about 20-25° C. for about 12 hours to provide a gel.

The resulting gel contained about 1 wt % Tobramycin as a mixture of a decanoic acid salt and oleic acid salt, about 1 wt % Terbinafine as a mixture of a decanoic acid salt and an oleic acid salt, about 0.1 wt % Betamethasone acetate, and about 0.02 wt % Benzethonium chloride, and exhibited a viscosity of about 7,170 cps at 25° C.

Example 8.5

Polymer-Solvent Pharmaceutical Composition of the Invention

About 63.0 grams of glycerol, followed by PEG 400 (about 398.2 g) and oleic acid (about 6.5 g), were added to a first flask and the resultant mixture of was stirred and heated to about 40° C. About 5.0 grams of Terbinafine, about 5.0 g of Florfenicol, about 500 mg of Betamethasone acetate, and about 100 mg of Benzethonium chloride were added to the mixture, and the resultant solution stirred for about 1 hour at a temperature of about 40° C. until clear.

In a 50 mL centrifuge tube was added about 12 g of PEG 400 followed by about 1.25 g of CARBOMER™ 941 (crosslinked poly(acrylic acid) polymer, commercially available from Noveon, Inc., of Cleveland, Ohio). The resultant mixture was mixed well using a vortex mixer and then combined with the contents of the first flask with stirring at a temperature of about 40° C. The steps of adding about 12 g of PEG 400 followed by about 1.25 g of CARBOMER™ 941 (crosslinked poly(acrylic acid) polymer, commercially available from Noveon, Inc., of Cleveland, Ohio) to a 50 mL centrifuge tube, mixing the resultant mixture well using a vortex mixer, and adding the resultant mixture to the contents of the first flask with stirring at a temperature of about 40° C. was repeated 2 more times. The contents of the first flask were then stirred for about 60 minutes at a temperature of about 40° C. The resulting contents of the first flask was then allowed to sit undisturbed at a temperature of about 20-25° C. for about 12 hours to provide a gel.

The resulting gel contained about 1 wt % Terbinafine as an oleic acid salt, about 1 wt % Florfenicol, about 0.1 wt % Betamethasone acetate, and about 0.02 wt % Benzethonium chloride, and exhibited a viscosity of about 35,480 cps at 25° C.

Example 8.6

Treatment of a Fungal Infection in a Human using a Pharmaceutical Composition of the Invention The pharmaceutical composition of Example 8.5 was administered to the foot of a 24 year-old male suffering from Athlete's foot. The pharmaceutical composition was administered once a week for 3 weeks. After 3 weeks, the subject noted a disappearance in symptoms of the fungal infection, such as reduced itching, redness, and inflammation.

Example 8.7

Stability of the Pharmaceutical Compositions

A pharmaceutical composition prepared as described in Example 8.1, was incubated at a temperature of about 40° C. or about 70° C. for up to 7 days to monitor the degradation of Terbinafine as a function of time and temperature. Only Terbinafine was monitored, since Terbinafine is known to be the least stable component of the pharmaceutical composition of Example 8.1. The concentration of Terbinafine was determined at each time point by the following HPLC procedure:

About 200 mg of the pharmaceutical composition is weighed into a 100 mL volumetric flask and the flask is filled to volume with about a 50:50 mixture of about 25 mM phosphate buffer at about pH 2.4 and about a 50:50 mixture of methanol:acetonitrile and shaken for about 1 minute. About 2 mL of the resulting solution is then filtered through an Acrodisc 25 mm syringe filter (0.2 µm Ultipore nylon membrane), and about 10 µL of the filtered solution is injected onto a Phenomenex Luna, 5 µm, C8 100A, 250 mm×4.6 mm, analytical HPLC column. The HPLC is operated at a flow rate of about 1 ml/min and eluted with about 50% of about 25 mM phosphate buffer at about pH 2.4 and about 50% of about a 50:50 mixture of methanol:acetonitrile for about 40 minutes. The HPLC is equipped with a UV detector. Terbinafine is detected at about 223 nm.

The results of the stability test is provided in Table 1.

TABLE 1

Stability of Terbinafine in the Pharmaceutical Composition of Example 8.1.

| Temperature (° C.) | Time (days) | % Degradation) |
|---|---|---|
| 40 | 1 | 1.1 |
| 40 | 2 | 1.2 |
| 40 | 3 | 2.8 |
| 40 | 4 | 1.8 |
| 40 | 5 | 1.2 |
| 40 | 6 | 1.5 |
| 40 | 7 | 2.2 |
| 70 | 1 | 1.1 |
| 70 | 2 | 1.2 |
| 70 | 3 | 1.8 |
| 70 | 4 | −0.3 |
| 70 | 5 | 1.9 |
| 70 | 6 | 3.0 |
| 70 | 7 | −17.2 |

The date in Table 1 shows that the pharmaceutical composition of Example 8.1 has good stability.

Example 8.8

Clinical Studies

Several dogs with ear infections were administered the pharmaceutical composition of Example 8.1 or 8.5.

The following protocol was followed to evaluate the clinical efficacy of the pharmaceutical compositions of the invention.

Dogs with ear infections were examined by a veterinarian on day 0, and each ear was assigned a clinical score based on the following signs related to otitis externa: pain, erythema, exudate, swelling, odor and ulceration. The following scale was used:

Pain: 0=none
   1=mild/moderate: painful on palpation
   2=severe: painful when raise the pinna
Erythema
   0=none
   1=mild/moderate: barely perceptible to obvious redness visible with otoscope
   2=severe: beet or cherry red or erythema extends into pinna
Exudate
   0=none
   1=mild/moderate: small amount visible in ear canal
   2=severe: extending out of ear canal and may be crusted
Swelling
   0=none
   1=mild moderate: some occlusion of ear canal
   2=severe: canal completely occluded
Odor
   0=none
   1=mild/moderate: malodor evident when pinna raised
   2=severe: malodor evident without raising pinna to expose ear canal
Ulceration
   0=none
   1=mild/moderate: mild abrasions
   2=severe: abrasions that may be bleeding The score for pain, erythema, exudate, swelling, odor and ulceration was combined to provide total clinical score ranging from 0 to 12 with 12 being the most severe otitis externa and 0 being the least severe otitis externa.

On day 0 the dog also received a physical exam, an ear swab was obtained to submit for a bacterial and yeast culture, and a second ear swab was obtained to prepare a roll smear to identify bacteria and/or yeast. The dogs ear was also cleaned with a cleansing solution free of antimicrobial and anti-inflammatory activity, and excess solution was removed from the ear. About 0.5 mL of the pharmaceutical composition of Example 8.1 or 8.5 was then administered to each infected ear and the ears massaged to distribute the pharmaceutical composition.

On day 7 (±2 days) a clinical score was again assigned to each ear using the same scale as used on day 0. On day 7 (±2 days) 0.5 mL of the same pharmaceutical composition as was administered on day 0 was again administered to each infected ear and the ears massaged to distribute the pharmaceutical composition.

On day 14 (±2 days) a clinical score was again assigned to each ear using the same scale as used on day 0.

Various breeds of dogs were used in the study of both sexes, various body weights, and physiological states. All dogs were at least about 8 weeks old and in general good health. For inclusion in the study the dogs had a minimum total clinical score on day 0 of about 6, received no treatment with systemic or otic antimicrobials or anti-inflammatories within the last month, had intact tympanic membranes, exhibited visualization of bacteria or yeast on the roll smear, and possessed no concurrent Otodectes cynotis infections.

The results of the study are provided below in Table II. Dogs in Group A were treated with the pharmaceutical composition of example 8.1 and dogs in Group B were treated with the pharmaceutical composition of example 8.5.

TABLE II

| | Score | | | | | |
|---|---|---|---|---|---|---|
| | Day 0 | | Day 7 | | Day 14 | |
| Animal No. | Left Ear | Right Ear | Left Ear | Right Ear | Left Ear | Right Ear |
| Group A[1] | | | | | | |
| 3 | 6 | 2 | 3 | 2 | 2 | 1 |
| 6 | 11 | 0 | 4 | 0 | 4 | 0 |
| 9 | 6 | 6 | 3 | 3 | 2 | 2 |
| 12 | 12 | 11 | 12 | 10 | 12 | 12 |
| Group B[2] | | | | | | |
| 2 | 8 | 4 | 3 | 3 | 2 | 1 |
| 5 | 12 | 12 | 7 | 8 | 2 | 3 |
| 8 | 6 | 8 | 5 | 5 | 5 | 5 |
| 11 | 8 | 9 | 1 | 2 | 5 | 5 |
| 14 | 12 | 0 | 9 | 0 | 12 | 0 |

[1]Dogs in Group A were treated with the pharmaceutical composition of example 8.1.
[2]Dogs in Group B were treated with the pharmaceutical composition of example 8.5.

The data in Tables II clearly shows that the pharmaceutical composition of the invention are effective at treating otic microbial infections in dogs.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those killed in the art and are intended to fall within the scope of the appended claims.

A number of references have been cited, the entire disclosure of which are incorporated herein by reference.

What is claimed is:

1. A method of treating or preventing a condition in an animal comprising topically, otically, or ophthalmically administering a therapeutically effective amount of a composition comprising:
   a solvent comprising glycerol formal;
   hydroxypropyl methylcellulose; and
   an antibacterial agent, an antifungal agent, and a steroid,
      wherein the antibacterial agent, antifungal agent, and steroid are dissolved in the solvent and the pharmaceutical composition is in the form of a gel.

2. The method of claim 1, wherein the animal is a nonhuman animal.

3. The method of claim 1, wherein the pharmaceutical composition is substantially free of water.

4. The method of claim 1, wherein the solvent further comprises a second organic solvent selected from the group consisting of glycerol, propylene glycol, poly(ethylene glycol), and mixtures thereof.

5. The method of claim 4, wherein the second organic solvent comprises glycerol.

6. The method of claim 4, wherein the second organic solvent comprises propylene glycol.

7. The method of claim 4, wherein the second organic solvent comprises poly(ethylene glycol).

8. The method of claim 1, wherein the antibacterial agent is Tobramycin or a pharmaceutically acceptable salt thereof the antifungal agent is Terbinafine or a pharmaceutically acceptable salt thereof and the steroid is Betamethasone or a pharmaceutically acceptable ester thereof.

9. The method of claim 8, wherein the Tobramycin or a pharmaceutically acceptable salt thereof is present in an amount ranging from about 0.5 to 3 wt %, the Terbinafine or a pharmaceutically acceptable salt thereof is present in an amount ranging from about 0.5 to 3 wt %, and the Betamethasone or a pharmaceutically acceptable ester thereof is present in an amount ranging from about 0.01 to 0.5 wt %.

10. The method of claim 1, wherein the antibacterial agent is Florfenicol or a pharmaceutically acceptable ester thereof, the antifungal agent is Terbinafine or a pharmaceutically acceptable salt thereof and the steroid is Betamethasone or a pharmaceutically acceptable ester thereof.

11. The method of claim 10, wherein the Florfenicol or a pharmaceutically acceptable ester thereof is present in an amount ranging from about 0.5 to 3 wt %, the Terbinafine or a pharmaceutically acceptable salt thereof is present in an amount ranging from about 0.5 to 3 wt %, and the Betamethasone or a pharmaceutically acceptable ester thereof is present in an amount ranging from about 0.01 to 0.5 wt %.

12. The method of claim 1, wherein the antibacterial agent is Gentamicin or a pharmaceutically acceptable salt thereof the antifungal agent is Clotrimazole or a pharmaceutically acceptable salt thereof, and the steroid is Betamethasone or a pharmaceutically acceptable ester thereof.

13. The method of claim 12, wherein the Gentamicin or a pharmaceutically acceptable salt thereof is present in an amount ranging from about 0.5 to 3 wt %, the Clotrimazole or a pharmaceutically acceptable salt thereof is present in an amount ranging from about 0.5 to 3 wt %, and the Betamethasone or a pharmaceutically acceptable ester thereof is present in an amount ranging from about 0.01 to 0.5 wt %.

14. The method of claim 1, wherein the amount of hydroxypropyl methylcellulose ranges from about 1 to about 4 weight percent of the composition.

15. The method of claim 14, wherein the amount of hydroxypropyl methylcellulose ranges from about 3 to about 4 weight percent of the composition.

16. A method of treating or preventing a condition in an animal comprising topically, otically, or ophthalmically administering a therapeutically effective amount of a pharmaceutical composition comprising:
a solvent comprising a first organic solvent selected from the group consisting of glycerol formal, ethyl lactate, and a mixture thereof;
hydroxypropyl methylcellulose in an amount ranging from about 1 to about 4 weight percent of the composition; and
an antibacterial agent, an antifungal agent, and a steroid, wherein the antibacterial agent, antifungal agent, and steroid are dissolved in the solvent; and the pharmaceutical composition is in the form of a gel.

17. The method of claim 16, wherein the amount of hydroxypropyl methylcellulose ranges from about 3 to about 4 weight percent of the composition.

* * * * *

UNITED STATES PATENT AND TRADEMARK OFFICE
CERTIFICATE OF CORRECTION

PATENT NO. : 7,622,138 B2  Page 1 of 1
APPLICATION NO. : 11/019243
DATED : November 24, 2009
INVENTOR(S) : Yerramilli V. S. N. Murthy It is certified that error appears in the above-identified patent and that said Letters Patent is hereby corrected as shown below:

Title page Assignee should read
Item (73) IDEXX Laboratories, Westbrook, ME (US)

Col. 30 Line 60 Claim 2 should read
2. The method of claim 1, wherein the animal is a non-human animal.

Col. 31 Line 7 Claim 8 should read
8. The method of claim 1, wherein the antibacterial agent is Tobramycin or a pharmaceutically acceptable salt thereof, the antifungal agent is Terbinafine or a pharmaceutically acceptable salt thereof, and the steroid is Betamethasone or a pharmaceutically acceptable ester thereof.

Col. 31 Line 19 Claim 10 should read
10. The method of claim 1, wherein the antibacterial agent is Florfenicol or a pharmaceutically acceptable ester thereof, the antifungal agent is Terbinafine or a pharmaceutically acceptable salt thereof, and the steroid is Betamethasone or a pharmaceutically acceptable ester thereof.

Col. 31-32 Line 31-35 Claim 12 should read
12. The method of claim 1, wherein the antibacterial agent is Gentamicin or a pharmaceutically acceptable salt thereof, the antifungal agent is Clotrimazole or a pharmaceutically acceptable salt thereof, and the steroid is Betamethasone or a pharmaceutically acceptable ester thereof.

Signed and Sealed this

Twelfth Day of January, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,622,138 B2 | Page 1 of 1 |
| APPLICATION NO. | : 11/019243 | |
| DATED | : November 24, 2009 | |
| INVENTOR(S) | : Yerramilli V. S. N. Murthy | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 819 days.

Signed and Sealed this

Twenty-sixth Day of October, 2010

David J. Kappos
*Director of the United States Patent and Trademark Office*